United States Patent [19]

Heusser et al.

[11] 4,191,740

[45] Mar. 4, 1980

[54] SYNTHETIC RESIN-BASE, ANTIBIOTIC COMPOSITIONS CONTAINING AMINO ACIDS

[75] Inventors: Dietrich Heusser; Elvira Dingeldein, both of Darmstadt, Fed. Rep. of Germany

[73] Assignee: Merck Patent Gesellschaft mit beschränkter Haftung, Darmstadt, Fed. Rep. of Germany

[21] Appl. No.: 845,703

[22] Filed: Oct. 26, 1977

[30] Foreign Application Priority Data

Nov. 11, 1976 [DE] Fed. Rep. of Germany ....... 2651441
Jun. 18, 1977 [DE] Fed. Rep. of Germany ....... 2727535

[51] Int. Cl.$^2$ .......................... A61K 9/16; A61L 15/03
[52] U.S. Cl. .......................................... 424/14; 424/28; 424/81; 128/92 B; 128/92 C; 128/114; 128/260; 3/1.9
[58] Field of Search ................. 424/28, 81, 14; 3/1.9; 128/92 B, 92 C, 114, 260

[56] References Cited

U.S. PATENT DOCUMENTS

| | | | |
|---|---|---|---|
| 2,430,740 | 11/1947 | Sharples | 424/28 |
| 3,868,447 | 2/1975 | Kliment | 424/81 |
| 3,955,566 | 5/1976 | Stoffey | 424/28 X |
| 4,059,684 | 11/1977 | Gross et al. | 424/81 X |
| 4,093,576 | 6/1978 | de Wijn | 424/81 X |

OTHER PUBLICATIONS

C.A. 82:103178m (1975), 81 #29549a (1974), 86 #34247b, #47277m, #47297t (1977).
C.A. 72 #3052r (1970), 83 #80295b (1975), 80 #1222y3d (1974).

*Primary Examiner*—Shep K. Rose
*Attorney, Agent, or Firm*—Millen & White

[57] ABSTRACT

By adding amino acids to antibiotic-containing compositions having as a base polymethacrylates, acrylates or a mixture thereof, reproducible improved antibiotic-release properties are achieved.

5 Claims, No Drawings

SYNTHETIC RESIN-BASE, ANTIBIOTIC COMPOSITIONS CONTAINING AMINO ACIDS

BACKGROUND OF THE INVENTION

The present invention is concerned with a composition containing an antibiotic and a synthetic resin material and with the use thereof especially in surgery.

It is known that antibiotics, especially gentamycin, are slowly liberated from synthetic resins based on polymethacrylates and/or polyacrylates. A sharp initial drop in concentration, due to the liberation of the antibiotic from the outermost layers of the synthetic resin, is followed by an almost constant rate of liberation which, however, decreases slowly over a long period of time. These antibiotic-containing synthetic resins have hitherto been used as bone cements for fixing endoprostheses, for example, total hip endoprostheses, and have been used during the changing of infected endoprostheses. For use in combating infection and for prophylaxis, the compositions are prepared by adding the antibiotic before complete polymerization of the synthetic resin. Furthermore, it is known that for this purpose, synthetic resin particles in the form of a granulate or of small spheroids with a particle diameter of 1 to 20 mm., are especially suitable as carrier materials for antibiotics.

Furthermore, it is known from German Pat. No. 2,511,122 that an antibiotic can be liberated from bone cement in comparatively high concentration when the bone cement additionally contains sodium chloride, potassium chloride, sodium bromide and/or potassium bromide. However, the use of these additional materials can cause problems since they have a cell-damaging effect. Therefore, for example, they are not to be used in surgery.

In addition, it has been shown that the liberation of the antibiotic from the synthetic resin particles does not take place in an optimum manner and can vary from one batch to another. Furthermore, in some production processes for such synthetic resin particles, temperatures can sometimes be reached at which some of the antibiotic can be decomposed. The destroyed amount is then no longer available for therapeutic purposes.

SUMMARY OF THE INVENTION

Accordingly, it is an object of the present invention to provide an antibiotic-containing composition having a synthetic resin particle base from which the antibiotic can be liberated in an optimum manner without danger of damage due to added materials.

This and other objects of this invention have been achieved by incorporating at least one amino acid in the antibiotic-containing synthetic resin composition.

Thus, in a composition aspect, the present invention relates to a composition comprising at least one antibiotic, polymethacrylate and/or polyacrylate based synthetic resin particles and at least one amino acid.

In a method of use aspect, the present invention relates to a method of administering antibiotics, especially for surgical uses such as those involving endoprostheses, which comprises administering a composition comprising at least one antibiotic, polymethacrylate and/or polyacrylate based synthetic resin particles and at least one amino acid.

In a method aspect, the present invention also provides a method for improving the liberation characteristics of antibiotics from antibiotic-containing synthetic resin particles based on polymethacrylates and/or polyacrylates, wherein 0.3 to 5% by weight, based on the amount of polymers, of at least one amino acid is added to the synthetic resin.

In a particularly preferred embodiment, the composition of this invention preferably contains essentially a copolymer of methyl methacrylate and methyl acrylate and gentamycin as the antibiotic. An especially advantageous embodiment results when the individual composition particles are connected together, at least partially, using filaments or wires.

Upon further study of the specification and appended claims, further objects and advantages of this invention will become apparent to those skilled in the art.

DETAILED DISCUSSION

Surprisingly, the liberation of an antibiotic from antibiotic-containing synthetic resin particles is substantially improved in the presence of amino acids. That is, with high reproducibility from batch to batch, a continuous, slowly decreasing liberation of the antibiotic can be achieved over a comparatively long period of time. Even a low concentration of physiologically compatible amino acids has this effect, and in contradistinction to the side effects observed when prior art additives were used, cell-damaging action does not occur. Furthermore, it has been surprisingly found that the stability of a bone cement with which the composition has been used is practically unimpaired by the addition of the amino acids.

The incorporation of amino acids in the composition improves the liberation characteristics thereof by permitting the release of the antibiotic in comparatively high concentrations without any harmful side effects.

In principle, all naturally-occurring and physiologically compatible amino acids can be used in the present invention. Amino acids which are not naturally-occurring can also be used as long as they are physiologically compatible. Especially good results are achieved with amino acids which have a water-solubility of about at least 1 g/100 ml. It is preferred to use aliphatic mono-aminomonocarboxylic acids containing up to 5 carbon atoms, for example glycine, alanine, threonine, valine, serine, hydroxyproline and proline. Glycine and alanine are preferred and glycine is especially preferred. The amino acids can be used alone or in mixtures.

The amount of amino acid or acids to be added can be varied within a wide range, the content depending, at least in part, upon the solubility of the amino acid or acids employed. In general, an addition of 0.3 to 5% by weight of amino acid or acids, referred to the polymer, is preferred. Most preferred is 0.5 to 2% by weight. When, for example, glycine is used, an addition of about 1% by weight has proved to be especially advantageous.

Synthetic materials for surgical purposes based on polymethacrylates and/or polyacrylates are known. For example, the polymers largely used as bone cements are particularly suitable. Such bone cements based on polyacrylates and/or polymethacrylates (usually designated as acrylic cement) are, for instance, available under the trademark PALACOS, especially PALACOS R, manufactured by KULZER & CO, Bad Homburg, Federal Republic of Germany; or C.M.W.—Bone cement, sold by C.M.W. Laboratories Ltd, Blackpool FY4 4QF; or Surgical Simplex P Radiopaque Bone Cement, marketed also in the United States.

For example, a conventional bone cement which is commercially available (PALACOS R) comprises two packs each containing about 40 g of powder, and 2 ampoules each containing 20 ml of liquid. The powder is a fine pearl polymer (particle diameter <30 μm) of a methyl methacrylate-methyl acrylate copolymer. About 0.5 weight % of dibenzoyl peroxide is added to the powder as a catalyst. For identification of the material, traces of chlorophyll can be polymerized in during production thereof. The powder can also contain, for example, zirconium dioxide as an X-ray contrast agent. The associated liquid consists of monomeric methyl methacrylate to which is added about 0.7 weight % of dimethyl-p-toluidine as an accelerator, as well as traces of hydroquinone as a stabilizer. As a rule, this liquid is also colored with traces of chlorophyll for identification purposes. The powder, which is packed into polyethylene packs, can be sterilized with ethylene oxide. The liquid can be sterilized by filtration and filled into glass ampoules.

Upon mixing together 2 parts by weight of powder with 1 part by weight of liquid, the dibenzoyl peroxide reacts with the dimethyl-p-toluidine in the liquid, thereby initiating the radical polymerization. The mixture is so adjusted that it can be used in the form of a paste after only about 1 minute. This paste remains kneadable for about 4 minutes and then begins to harden, with the evolution of heat. After 6 minutes, the polymerization is substantially complete. When used as bone cement or bone putty, the pliable paste is molded with the parts to be connected and, as a rule, hardens in situ. However, the forming and the hardening can also take place outside of the body, the formed parts then being introduced into the body during or after hardening.

Suitable synthetic resins for use in the present invention, however, are also available in completely polymerized form. These are preferably employed in the form of a pearl polymer. When using the composition of this invention for the production of bone cements, especially for endoprostheses, as well as for implantable formed bodies, it is advantageous to start from a pearl polymer of synthetic resin particles having particle diameters of <30 μm. This pearl polymer can also be used for the production of synthetic resin particles having larger particle diameters, e.g., 1 to 20 mm. If desired, the individual particles can be connected together, at least in part, with the help of filaments or wires. Injection molding can also be used to form such sized particles. Consequently, the necessary working temperatures are considerably reduced so that only mild working conditions need be used, thereby greatly lessening the likelihood that the antibiotic would be damaged.

Suitable particle diameters can be from 1 to 20 mm, and preferably from about 7 to 10 mm. The granulate or the material in the form of spheroids can be produced not only immediately before an operation, but can also be obtained in storable finished form. Of course, care must always be taken to ensure sterility.

According to a special embodiment of the present invention, the particles are connected together with filaments or wires. For example, while the material is still in a moldable state, it can be strung like pearls onto a filament or wire. Alternately, a filament or wire can be pressed into the material. The filament can be any suitable conventional surgical stitching material or a high alloy steel wire, as in conventionally used in bone surgery. The composition of this invention in this form has the advantage that it is simple to handle during an operation and, in case of a re-operation, can be readily removed. Moreover, for first aid purposes, a temporary filling can also be made in this manner. The wires are also X-ray contrastable. Thus, for example, when necessary or desirable, removal of the particles from enveloping connective tissue is made simpler. The temporary introduction of the composition of this invention into a narrow cavity is also possible, for example, after removal of a bone pin because of marrow cavity phlegmons.

In principle, all antibiotics can be used as long as they are not damaged at the temperatures which occur during polymerization or sintering of the composition, and are liberated from the synthetic resin in the desired manner. Furthermore, the antibiotics should be chemically stable towards the synthetic resin.

Their spectrum of activity should include gram-positive or gram-negative microorganisms or preferably both groups of microorganisms. If possible, the microorganisms should have a retarded resistance development with regard to the antibiotics employed. From the large number of antibiotics which can be used, by way of example, the following are suitable: erythromycin, lincomycin, clindamycin, novobiocin, vancomycin, fusidic acid, rifamycin, polymyxins, neomycin, kanamycin, tobramycin and, in particular, gentamycin. Penicillins and cephalosporins can also be used. Because of their broad antibacterial spectrum and their heat stability, the aminoglycoside antibiotics are especially preferred.

The amount of added antibiotic can be varied within wide limits and depends essentially upon the activity of the antibiotic. In general, suitable amounts of antibiotic range from about 0.2 to 15% by weight, referred to the polymer. In the case of gentamycin, for example, additions of from 1 to 4% by weight, calculated as gentamycin base, have proven to be especially useful. The other antibiotics are preferably also used in amounts of adequate antimicrobial activity.

To the available commercial packs (PALACOS R) containing partially polymerized synthetic resin, there can be added, for example, 0.5 to 1 g of gentamycin for about 6 g of polymer (40 g of powder and 20 ml of liquid). However, other amounts of antibiotics or other mixtures of antibiotics can also be selected. Thus, for example, a substantially higher proportion can be used when a comparatively small cavity is to be filled but, nevertheless, a particularly effective dose of the antibiotic is to be introduced. Whenever a second, different antibiotic is needed, e.g., if the cause of infection or the resistance to the incorporated antibiotic changes, the composition of this invention can be easily removed and optionally replaced by another one containing one or more different antibiotics.

For the production of the composition of the present invention, at least one antibiotic and at least one amino acid is incorporated into the synthetic resin. The incorporation can be performed using any suitable conventional method. For example, it can be effected by introducing both components into the synthetic resin before hardening thereof or by intensively mixing them with an already polymerized product, for example, a pearl polymer. Alternatively, one component can be pre-incorporated in the pearl polymer and the other component(s) can subsequently be incorporated therewith by mixing. The mixes are then shaped as desired in any conventional way.

The compositions of the present invention are especially suitable for the prevention of infection in heavily contaminated and extensive wounds in soft tissues, or in damaged tissues attendant to compound bone fractures such as frequently occur as a result of accidents. They can be used to temporarily fill a potentially infected wound having contaminated skin closure. It is thus possible to apply antibiotics locally in depot form, i.e., directly to the infected or endangered places. In addition, the application can be discontinued as desired or can be repeated in any desired manner. For comparatively large wounds, it is especially simple to introduce the composition in the form of particles which are connected together as described above, since then all the particles can subsequently be readily removed, for example, by pulling on one end of the filament.

An additional important field of use is bone surgery, especially in the treatment of post-traumatic osteomyelitis. The new agent is suitable for filling osteomyelitic cavities. Surprisingly, connective tissue grows into the interstices between the synthetic resin particles. Thus, in spite of infection, the material is incorporated as in an aseptic medium. The composition of this invention can also be used for the provision of an aseptic transplant site for a possible subsequent introduction of spongiosa from the patient's own body. Alternatively, it can be used for the open filling of osteomyelitic cavities when a primary skin closure is not possible. The uppermost layer of the particles can be subsequently removed when the underlying particles are substantially enveloped by connective tissue so that a skin transplant is possible.

The compositions of the present invention can, in particular, also be used for anchoring joint endoprostheses, for the firm bonding of bones, for cementing in implants and for similar surgical procedures. However, they can also be used in the form of implantable formed bodies, complete hardening taking place inside or outside the body.

The new surgical composition is especially advantageous when the synthetic resin is completely hardened before introduction into the body. In this case, there is no evolution of heat in the bone tissue due to complete polymerization, which means that the operation can be carried out under milder conditions. Moreover, for extracorporeally hardened synthetic resins, the danger that residual monomers would be liberated during the operation is reduced, so that a potential risk with regard to the heart-circulatory system does not arise. The new surgical material is preferably used for the prevention of infection or boundary surfaces between bone cement and bone, or between endoprosthesis and tissue. It is also used in wounds in soft tissues or in compound fractures, as well as for the treatment of chronic osteomyelitis. When carrying out an operation, the powdered pearl polymer, which contains the antibiotic and the amino acid, is mixed with the monomer-containing liquid. The plastic paste obtained is introduced into the body and molded in the desired manner. Alternatively, a molded body can be produced from the bone cement and then implanted into the body. An additional technique is to carefully fill the wound activity with the composition or to introduce the spheroids attached to filaments or wires. By appropriate selection of the dimensions of the particles in conventional fashion, an optimum filling of the cavities can be achieved. The new material has proved to be outstandingly useful in numerous operations.

When used for the treatment of osteomyelitis, a very rapid overcoming of the putrescent secretion is observed. Open cavities filled with the composition of this invention appear to be completely free of irritation and display no inflammatory phenomena. As an indication of the lack of infection, the particles are slowly enveloped by connective tissue. As an added feature, the position of the particles can be very readily monitored since the synthetic particles can clearly be recognized by X-ray detection. A preferred antibiotic is, for example, gentamycin. It is an aminoglycoside antibiotic which acts primarily bactericidally against gram-positive but especially against gram-negative microorganisms. Since all of these microorganisms can sustain a chronic osteomyelitis, this antibiotic has been used in the past for treatment of osteomyelitis, taking advantage of its local and systemic action. According to the present invention, by the addition of amino acids, an improved liberation of gentamycin is achieved, particularly from synthetic resins based upon polymethacrylates and/or polyacrylates. Apparently because of the very good water-solubility of this antibiotic very favorable diffusion from the synthetic resin occurs, especially in the presence of an amino acid, such as glycine. After an initial drop of concentration, the high diffusability permits an almost constant rate of liberation which decreases only slowly over an extraordinarily long period of time. In this manner, sufficient antibiotic protection is ensured even after several months. This is a great advantage in comparison with the previously used treatment techniques in which the amount of antibiotic liberated generally varies quite greatly. Furthermore, due to the nature of the added amino acids, tissue cell damage is avoided.

The methods used to prepare the composition of this invention and the considerations involved in selecting appropriate parameters such as particle size, etc., are completely conventional. These are described, for example, in U.S. Pat. No. 3,882,858 and German Pat. No. 2,511,122.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

40 g of a sterile, fine pearl polymer (particle diameter $<30$ $\mu$m), consisting of a copolymer of methyl methacrylate and methyl acrylate, which additionally contained 0.5% of dibenzoyl peroxide, traces of chlorophyll and 15% zirconium dioxide as an X-ray contrast agent, were mixed well with 0.5 g of gentamycin sulphate and 0.4 g of glycine. The powder obtained was then mixed with 20 ml of a liquid which consisted of monomeric methyl methacrylate containing about 0.7% of dimethyl p-toluidine and about 0.006% of hydroquinone. From the paste obtained after thorough mixing, there were formed spheroids with a diameter of about 7 mm. After about 6 minutes, the particles were hardened. A sterilization, for example by gassing with ethylene oxide, could, if desired, be employed. The resultant spheroids can be used for the prevention of infection in wounds in soft tissue or in the zones of destruction attendant to compound fractures, or also for filling osteomyelitis cavities.

EXAMPLE 2

In a manner analogous to that described in Example 1, spheroids were formed with a diameter of about 7 to 10 mm. To 60 g of polymer there were added 1 g of gentamycin sulphate and 0.6 g of glycine. Before complete hardening, the resultant particles were strung, at a spacing of about 2 mm, like pearls on a filament (surgical high-alloy steel) with a diameter of about 0.1 mm. The spheroids were then allowed to harden in this state. When used, the "string of pearls" can be cut off in any desired length.

EXAMPLE 3

40 g. of a sterile fine pearl polymer (particle diameter $<30$ μm), consisting of a copolymer of methyl methacrylate and methyl acrylate, which contained about 15% of zirconium dioxide as an X-ray contrast agent, were mixed well with 0.5 g of gentamycin sulphate and 0.4 g of glycine. The powder obtained was sintered in an appropriate apparatus and formed into appropriate shapes (preferably by injection molding). The incorporation of filaments or wires can also be accomplished at the same time. If desired, sterilization, for example by gassing with ethylene oxide, can follow. The spheroids can then be used for the prevention of infection in wounds in soft tissues or in the zones of destruction attendant to compound fractures, or also for filling osteomyelitic cavities.

EXAMPLE 4

In a manner analogous to that described in Example 1, a paste can be produced from the given components. This paste is employed in conventional manner as a bone cement for fixing endoprostheses in hip joint operations.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modification of the invention to adapt it to various usages and conditions.

What is claimed is:

1. A pharmaceutical composition consisting essentially of a base of fine pearl polymer spheroid, particles having diameters of 1–20 mm of methyl methacrylate-methyl acrylate copolymer, at least one antibiotic selected from gentamycin, erythromycin, lincomycin, clindamycin, novobiocin, vancomycin, fusidic acid, rifamycin, polymyxins, neomycin, kanamycin and tobramycin in antimicrobial amounts of about 0.2–15% by weight and an antibiotic-liberating agent, wherein the antibiotic liberating agent consists essentially of 0.3–5% by weight of at least one aliphatic, monoamino, monocarboxylic amino acid containing up to 5 carbon atoms selected from glycine, alanine, threonine, valine, serine, hydroxyproline, proline and mixtures thereof.

2. The composition of claim 1, wherein the amount of antibiotic is 0.2 to 15 weight %, based on the polymer.

3. The composition of claim 1, wherein the amino acid is glycine in a content of about 1% by weight.

4. The composition of claim 1, wherein the antibiotic is gentamycin.

5. The composition of claim 1, wherein the particles have a diameter of from 7 to 10 mm.

* * * * *